United States Patent
He et al.

(10) Patent No.: US 6,492,571 B1
(45) Date of Patent: Dec. 10, 2002

(54) PROCESS FOR ALKYLATION OF ISOPARAFFIN WITH OLEFIN

(75) Inventors: Yigong He, Bejing (CN); Yufeng He, Bejing (CN); Wenhua Xie, Bejing (CN); Qiang Fu, Bejing (CN)

(73) Assignees: China Petroleum Corporation, Beijing (CN); Research Institute of Petroleum Processing, Sinopec, Beijing (CN)

( * ) Notice: Subject to any disclaimer, the term of this patent is extended or adjusted under 35 U.S.C. 154(b) by 0 days.

(21) Appl. No.: 09/620,307

(22) Filed: Jul. 20, 2000

(30) Foreign Application Priority Data

Jul. 22, 1999 (CN) ........................ 99110816 A

(51) Int. Cl.[7] ............... C07C 2/00; C07C 2/56; C07C 2/58
(52) U.S. Cl. .............. 585/710; 585/704; 585/721; 585/722; 585/726; 585/730
(58) Field of Search ................ 585/704, 710, 585/721, 722, 726, 730

(56) References Cited

U.S. PATENT DOCUMENTS

| | | | |
|---|---|---|---|
| 3,855,343 A | 12/1974 | Huang et al. | 585/726 |
| 3,917,738 A | 11/1975 | Fenske et al. | 585/722 |
| 3,962,133 A | 6/1976 | Rodewald | 502/168 |
| 4,116,880 A | 9/1978 | Olah | 502/168 |
| 4,384,161 A | 5/1983 | Huang | 585/722 |
| 5,012,033 A | 4/1991 | Child et al. | 585/722 |
| 5,120,897 A | 6/1992 | Del Rossi et al. | 585/726 |
| 5,157,196 A | 10/1992 | Crossland et al. | 585/720 |
| 5,157,197 A | 10/1992 | Cooper et al. | 585/726 |
| 5,190,904 A | 3/1993 | Crossland et al. | 502/85 |
| 5,220,095 A | 6/1993 | Hommeltoft et al. | 585/720 |
| 5,221,777 A | 6/1993 | Huss, Jr. et al. | 585/726 |
| 5,245,101 A | 9/1993 | Del Rossi et al. | 585/726 |
| 5,288,685 A | 2/1994 | Kallenbach et al. | 502/168 |
| 5,324,881 A | 6/1994 | Kresge et al. | 585/721 |
| 5,326,923 A | 7/1994 | Cooper et al. | 585/725 |
| 5,346,676 A | 9/1994 | Crossland et al. | 422/211 |
| 5,364,976 A | 11/1994 | Kallenbach | 568/647 |
| 5,365,010 A | 11/1994 | Rao et al. | 585/726 |
| 5,391,827 A | 2/1995 | Koyama | 86/600 |
| 5,475,178 A | 12/1995 | Del Rossi et al. | 585/455 |
| 5,489,729 A | 2/1996 | Benazzi et al. | 585/731 |
| 5,489,732 A | 2/1996 | Zhang et al. | 585/467 |
| 5,491,278 A * | 2/1996 | Angstadt et al. | 585/731 |
| 5,523,503 A | 6/1996 | Funk et al. | 585/446 |
| 5,731,256 A | 3/1998 | Benazzi et al. | 502/202 |
| 5,739,074 A | 4/1998 | Kocal et al. | 502/227 |
| 5,811,626 A * | 9/1998 | Joly et al. | 585/731 |

FOREIGN PATENT DOCUMENTS

| | | |
|---|---|---|
| CN | 1184797 A | 6/1998 |
| EP | 0714871 A1 | 6/1996 |
| GB | 1389237 | 4/1975 |
| GB | 1432720 | 4/1976 |
| JP | 01245853 A | 10/1989 |
| JP | 08281118 A | 10/1996 |
| WO | WO 92/04977 A1 | 4/1992 |
| WO | WO 95/26815 A1 | 10/1995 |

* cited by examiner

Primary Examiner—Thuan D. Dang
(74) Attorney, Agent, or Firm—Morrison & Foerster LLP

(57) ABSTRACT

This invention relates to a process for alkylation of an isoparaffin with an olefin over a solid-acid catalyst, wherein at least two parallel reactors are used at the same time. When the solid acid catalyst in one or more reactors need to be regenerated, the catalyst is contacted in-situ in the reactor with a solvent to wash out the macromolecular hydrocarbons deposited on the surface of the catalyst in order to resume the high selectivity of catalyst in alkylation.

21 Claims, 3 Drawing Sheets

PROCESS FOR ALKYLATION OF ISOPARAFFIN WITH OLEFIN

FIELD OF THE INVENTION

The present invention relates to a process for alkylation of an isoparaffin with an olefin, especially alkylation of isobutane with butene over the solid acid catalysts.

BACKGROUND OF THE INVENTION

In petroleum-chemical industry, as well known in the art, concentrated sulfuric acid and hydrofluoric acid catalysts are widely used in the process of isoparaffin-olefin alkylation, especially in alkylation of isobutane with butene, in order to produce higher molecular weight alkylates with high octane rating, as valuable gasoline blending components. However, both sulfuric acid and hydrofluoric acid share inherent drawbacks including equipment corrosion problem, serious environment and safety concerns. A lot of efforts have been directed to developing solid acid alkylation process to substitute for sulfuric acid or hydrofluoric acid processes.

In the past, new solid acid catalysts for the above alkylation process have been widely investigated and reported. For example, JP 01, 245, 853, U.S. Pat. Nos. 3,962,133 and 4,116,880, GB 1,432,720 and GB 1,389,237, etc. disclose $SO_4^{2-}$ enhanced super acid catalysts; U.S. Pat. Nos. 5,220, 095, 5,731,256, 5,489,729, 5,364,976, 5,288,685 and EP 0,714,871A, etc. disclose $CF_3SO_3H$/silica catalysts; U.S. Pat. Nos. 5,391,527, and 5,739,074, etc. disclose Pt—$AlCl_3$—$KCl/Al_2O_3$ catalysts; U.S. Pat. Nos. 5,157,196, 5,190,904, 5,346,676, 5,221,777, 5,120,897, 5,245,101, 5,012,033, 5,157,197, CN 1,062,307A and WO 95,126,815, etc. disclose Lewis acid catalysts, such as $SbF_5$, $BF_3$ and $AlCl_3$; CN1, 184,797A, U.S. Pat. Nos. 5,324,881 and 5,475, 178, etc. disclose supported heteropoly acid catalysts; U.S. Pat. Nos. 3,917,738 and 4,384,161, etc. disclose molecular sieve catalysts.

The most serious problem existing in the solid acid alkylation process is that the catalysts deactivate very quickly during the reaction. For example, the deactivation of some molecular sieve catalysts and $SO_4^{2-}$/oxide catalysts occurs very quickly, in a few hours or even less than an hour, and the activity and selectivity of catalysts reduce dramatically resulting in the decline in the octane number of alkylate. Therefore, the regeneration of the solid acid alkylation catalysts has become a problem demanding prompt solution in the development of the solid acid alkylation process.

Presently, some kinds of hydrocarbon conversion reaction using solid acid catalysts, such as alkylation, isomerization, oligomerization and hydro-isomerization, are carried out at lower temperatures, wherein the macromolecular paraffins or olefins deposited on the surface of catalysts due to certain the side reactions, such as polymerization of olefin and hydride transference. These heavy hydrocarbons are organic compounds with a C/H ratio of less than 1, known as coke precursors, which are different from those coke substances with a C/H ratio of more than 1 originating in the reactions of hydrocarbon conversion at higher temperature, such as catalytic reforming and fluid catalytic cracking.

U.S. Pat. No. 5,365,010 discloses a process for regeneration of solid acid alkylation catalysts by calcination at high temperatures. In this process, Lewis acid catalysts, especially the $BF_3$ supported on alumina ($BF_3/Al_2O_3$), are calcinated at 600° C. in order to burn out the heavy hydrocarbons deposited on the surface of the catalysts. High temperature regeneration is only applicable to the catalysts having good high temperature stability.

U.S. Pat. No. 5,326,923 and CN 1,076,386A disclose a process for regeneration of hydrocarbon conversion catalysts comprising contacting supported Lewis acid catalysts with solvent $SO_2$ in order to remove the reaction deposits from the surface of the catalysts, and to reactivate the catalysts.

JP 8-281,118 discloses a method for regeneration of solid heteropoly acid catalysts, comprising extracting the solid heteropoly acid or salt alkylation catalysts outside the reactor at normal temperature and pressure with polar or non-polar solvents in order to reactivate the catalyst partly. The non-polar solvents of $C_4$–$C_{10}$ saturated fatty hydrocarbons are stated in the claims, but only polar solvents are used in the examples.

U.S. Pat. No. 3,855,343 discloses an isoparaffin-olefin alkylation process carried out in a slurry-phase reactor, comprising contacting isoparaffin with olefin in the presence of a $BF_3$-containing cation-exchange resin catalyst and regenerating the catalyst by extraction with polar solvents.

U.S. Pat. No. 5,489,732 discloses a moving-bed alkylation process in which the catalysts are regenerated by the following method: dividing the exhausted catalyst equally into two parts, regenerating one part of the catalysts with the liquid-phase isoparaffin feedstock containing dissolved $H_2$ and regenerating the other part of the catalysts with $H_2$ at high temperature, then combining the two parts of used catalysts and separating hydrogen out, then mixing with the feedstock and recycling into the reactor for alkylation.

U.S. Pat. No. 5,523,503 discloses a solid acid catalyst alkylation process using the cocurrent simulated moving-bed. The process is carried out in several beds divided into reaction zone and regeneration zone; in which the position of reaction zone and regeneration zone is changed by controlling the inlet points of the feedstocks and regeneration stream, thus the purpose of continuous reaction-and-regeneration is realized by the cycle of such switching-over. Wherein the feedstock in reaction zone passes through at least two catalyst beds, that is, the reaction effluent containing unreacted feedstock and products from the first reaction bed enters the second bed, or then enters the third bed. The solvent for regeneration of the catalyst is the liquid-phase isoparaffin feedstock containing dissolved $H_2$. In the process hydrogen needs to be separated. Moreover, there is at least one bed undergoing regeneration at any one time.

SUMMARY OF THE INVENTION

An object of the present invention is to provide an isoparaffin-olefin alkylation process to produce alkylated oils with high octane number, wherein the continuous alkylation reaction can be realized and at the same time the catalyst can be regenerated effectively to resume its alkylation activity and selectivity by a simple operational process without a regeneration zone undergoing regeneration at any one time.

The present invention provides a process for alkylation of isoparaffin with olefin using a solid acid catalyst, comprising:

Feeding an alkylation feedstock comprising isoparaffin and $C_3$~$C_6$ mono-olefins into at least two parallel reactors the reaction under conditions for alkylation in presence of a solid acid catalyst;

When the selectivity and activity of the catalyst in one or more of said reactors or the octane number of alkylate from the bottom descends due to macromolecular hydrocarbons deposited on the surface of the catalyst, switching said one or more reactors over to feed a solvent stream for regeneration of the catalyst to carry out the solvent extraction for regeneration of the catalyst in situ, and after the regeneration transferring the used solvent stream to the solvent-recovery unit for reuse;

Switching said one or more reactors over after the completion of the regeneration to feed said alkylation feedstock to continue the alkylation again;

Wherein the alkylation is being carried out in at least one of all reactors during the process.

DETAILED DESCRIPTION OF THE INVENTION

The invention provides a process for alkylation of isoparaffin with olefin over a solid acid catalyst. In the present process, the catalyst is regenerated in situ with a solvent, and at least two parallel reactors are used at the same time, each of which is charged with said catalyst and can be used for alkylation. Either the alkylation feedstock or the solvent for regeneration can pass through the inlet of each reactor by switching over the valves, and either the reaction effluent or the used solvent can pass through the outlet of each reactor to the fractionating tower of reaction products or to the recovery tank of recycling used solvents respectively by switching over the valves. The process can be described, as follows: Alkylation feedstock comprising isoparaffin and $C_3$~$C_6$ mono-olefins is fed into each reactor to carry out the reaction under the conditions for alkylation and then the reaction effluent flows into the fractionating tower, where the reaction products are separated out and the unreacted isoparaffin from the top of tower is circulated back to the reactors; when the selectivity and activity of catalyst in one or more of said reactors or the octane number of alkylates from the bottom descends due to macromolecular hydrocarbons deposited on the surface of the catalyst, said one or more reactors is/are switched over to feed a solvent stream for regeneration of the catalyst to carry out the regeneration-extraction of the catalyst, and thereafter the used solvent is transferred to the solvent-recovery tank, and as the regeneration is completed, said one or more reactors is/are switched over to feed the alkylation feedstock to carry out the alkylation again. The alkylation is carried out in at least one of said reactors during the process.

According to the process provided by the present invention, preferably, said isoparaffin is isobutane and said $C_3$~$C_6$ mono-olefin is butene.

According to the process provided by the present invention, said catalyst is a solid acid catalyst used widely in the prior art for alkylation of low-carbon isoparaffins with $C_3$~$C_6$ mono-olefins, such as supported heteropoly acid and salt catalysts, zeolite molecular sieve catalysts, $SO_4^{2-}$/oxide super acid catalysts, supported conjugated Brönsted-Lewis solid super acid catalysts, ion-exchange resin catalysts and Lewis acid-treated oxide or molecular sieve catalysts, etc. Since the deposits on the surface of the solid acid catalyst which cause the catalyst deactivation are the coke precursors with a C/H ratio of less than 1, a person having ordinary skill in the art is not difficult to understand that all the solid acid catalysts used for the alkylation of low-carbon isoparaffins with olefins can be regenerated by the process according to the present invention, so it is unnecessary to specify the catalysts particularly. Preferably the catalyst is one selected from the supported heteropoly acids catalyst, supported conjugated Brönsted-Lewis solid super acid catalysts or solid polymerized ion-exchange resin catalysts; and most preferably it is supported heteropoly acids catalysts.

According to the process provided by the present invention, said supported heteropoly acids catalyst comprises a porous inorganic supporter and a heteropoly acid having a chemical formula of $H_{8-n}[AM_{12}O_{40}]$, wherein A is phosphorus atom or silicon atom, M is tungsten atom or molybdenum atom, n is the number of valence state of A, being 4 or 5; said porous inorganic supporter material is a conventional one selected from the group consisting of active carbon, silica, alumina, magnesia, titanium oxide, crude or synthetical zeolites, carbon fiber and clay or mixtures thereof. Preferably it is selected from silica, alumina or the mixture thereof.

According to the process provided by the present invention, said supported conjugated Brönsted-Lewis solid super acid catalyst preferably comprises a porous inorganic supporter material of 40–95 wt %, a heteropoly acid of 1–60 wt % and a Lewis acid of 0.3~15 wt % supported thereon; said heteropoly acid and porous inorganic supporter material are the same as the ones defined in supported heteropoly acid catalysts as above; said Lewis acid is one selected from $AlCl_3$, $BF_3$ or $XF_5$, wherein X is P, As, Sb, or Bi.

According to the process provided by, the present invention, said other catalysts are conventional solid acid catalysts disclosed in the prior art for alkylation of low-carbon isoparaffins with olefins, and are not particularly specified in this invention.

According to the process provided by the present invention, said solvent for regeneration can be selected from a wide range of solvents, preferably at least one of non-polar solvents selected from the group including $C_4$~$C_{20}$ saturated fatty hydrocarbons and aromatics, etc., more preferably isobutane or $C_4$–$C_{16}$ saturated fatty hydrocarbons, and most preferably $C_5$–$C_{12}$ saturated fatty hydrocarbons, and/or at least one of polar solvents selected from the group including alcohols, phenols, ethers, esters, halide alkanes and $CS_2$, etc.; more preferably $C_2$–$C_8$ alcohols, $C_2$–$C_8$ esters or $C_1$–$C_4$ halide alkanes. It is worth mentioning that a non-polar solvent should be used for the regeneration of supported heteropoly acid alkylation catalysts because heteropoly acid may possibly be dissolved in a polar solvent.

According to the process provided by the present invention, said conditions for alkylation are those adopted widely in the alkylation process, preferably the supercritical reaction conditions, which include: a reaction temperature in the range of from the supercritical temperature of isoparaffin to 300° C., preferably from the supercritical temperature of isoparaffin to 250° C., and more preferably from the supercritical temperature of isoparaffin to 200° C.; a reaction pressure in the range of from the supercritical pressure of isoparaffin to 10.0 MPa, preferably from the supercritical pressure of isoparaffin to 9.0 MPa, and more preferably from the supercritical pressure of isoparaffin to 6.0 MPa; a mole ratio of isoparaffin to olefin in the range of 2.0~100, preferably 10~90; and a WHSV of feed in the range of 0.1~20 $hr^{-1}$, preferably 0.5~8 $hr^{-1}$.

According to the process provided by the preset invention, said process of solvent extraction of regeneration of the catalyst comprises separating the alkylation feedstock and catalyst in reactor, then introducing the solvent stream into the reactor and washing in-suit the catalysts with said solvent for 0.2~24 hrs, preferably 0.5~15 hrs under the conditions of temperature 25~300° C., preferably 50~200° C., pressure 0~8.0 MPa, preferably 0.2~6.0 MPa, and WHSV 0.1~20.0 $hr^{-1}$, preferably 0.5~8.0 $hr^-$.

According to the present invention, the process for alkylation of isoparaffin with olefin can be carried out in all kinds of reactors, such as the fixed-bed, batch-bed, moving-bed, and fluidized-bed reactors or the tri-phase slurry bed reactor, etc. The feedstock can flow either upward or downward.

The amount of extraction solvent used should be sufficient for totally or partly washing out the macromolecular hydrocarbons deposited on the surface of catalyst, which are organic compounds with C/H ratio less than 1. According to our study, it is learned that said macromolecular hydrocarbons deposited on the surface of the supported heteropoly acid alkylation catalyst are made up of $C_{13}$~$C_{25}$ saturated alkanes and a trace of polynuclear aromatic hydrocarbons.

The present invention will be further described with reference to the following samples. However, these examples are not to be construed to limit the scope of the present invention.

EXAMPLE 1

An isobutane-butene alkylation was carried out according to the process provided by the present invention, and aged catalyst was regenerated with solvent by washing and extracting in order to get rid of the macromolecular hydrocarbons deposited on the surface of the catalyst, while the cycle of alkylation and regeneration continued.

5.24 g of $H_3PW_{12}O_{40} \cdot 22H_2O$ (analytical grade, manufactured by Beijing Chemical Plant) was dissolved in 35 ml de-ionized water to form a $H_3PW_{12}O_{40}$ solution. 18.5 g 20~40 mesh silica (manufactured by Qingdao Ocean Chemical Plant) was put in a vacuum vessel and treated under 0.095 MPa and 75° C. for 1 hour, cooled to room temperature and added $H_3PW_{12}O_{40}$ solution under vacuum to impregnate for one hour, then dried at 160° C. for 6 hours (still under vacuum). A supported heteropoly acid catalyst comprising 20 wt % $H_3PW_{12}O_{40} \cdot 2H_2O$ and 80 wt % silica was obtained and designated as 20% $H_3PW_{12}O_{40} \cdot 2H_2O/SiO_2$. Said catalyst had a surface area of 350 $m^2/g$ as determined by low temperature nitrogen adsorption BET method.

10.0 g of said 20% $H_3PW_{12}O_{40} \cdot 2H_2O/SiO_2$ catalyst was loaded in a fix-bed reactor (50 ml) and was heated in a stream of dry nitrogen to the temperature and pressure required for alkylation. The feedstock with fixed mole ratio of isobutane to butene was pumped into the reactor by two precision metering pumps and the nitrogen steam was switched off at the same time. Vent was analyzed by HP-3420 gas chromatograph (with a chromatographic column of 50 m×0.2 mm OV-01 capillary cross-linked column) and the compositions of liquid alkylate were analyzed by HP-5890 gas chromatograph at regular intervals. The reaction was carried out under the conditions of a mole ratio of a isobutane to butene of 25.0, WHSV of 2.5 $hr^{-1}$, a reaction pressure of 4.0 MPa and a temperature of 145° C.

Compositions of isobutane-butene feedstock were the same for all of examples as listed in Table 1, but said mole ratio of isoparaffin to mono-olefin was the actual ratio of isobutane to butene with single double after mixed together.

TABLE 1

| composition of isobutane feed (w %) | | composition of butene feed (w %) | |
|---|---|---|---|
| propane | 2.31 | 1-butene and isobutene | 2.91 |
| isobutane | 95.1 | n-butane | 11.54 |
| n-butane | 1.54 | cis-butene-2 | 59.03 |
| butene | 1.95 | trans-butene-2 | 25.66 |
| | | isobutane | 0.86 |
| impurities | | impurities | |
| $H_2O$ | 34 ppm | $H_2O$ | 40 ppm |
| S | <1.0 $mg/m^3$ | S | <1.0 $mg/m^3$ |
| butadiene | 75 ppm | butadiene | 5 ppm |

Figure 1:
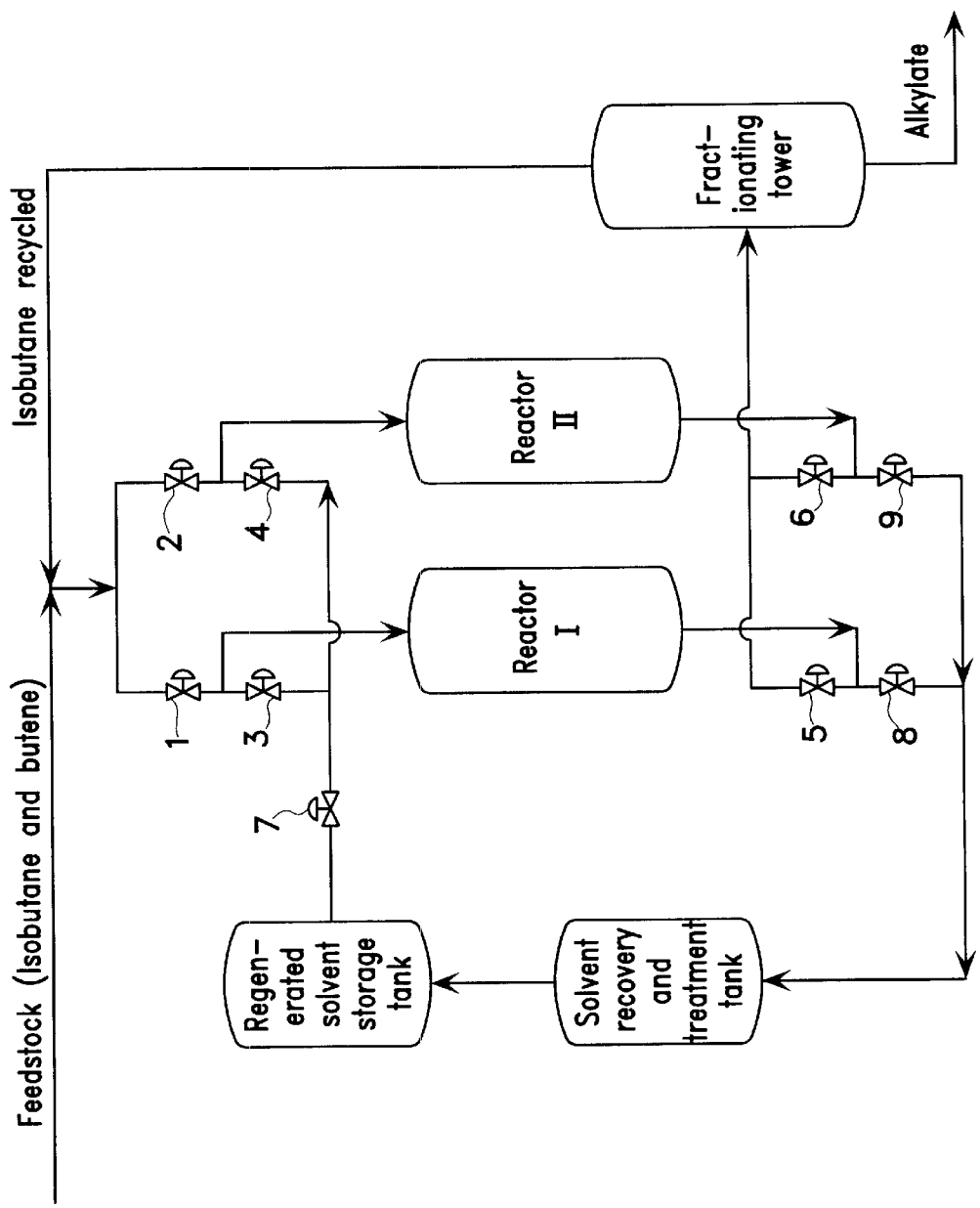
FIG. 1 shows a flow diagram of the alkylation process according to an embodiment of the present invention comprising two reactors. Alkylation feedstock containing isobutane and butene enters the reactors I and II while valves 3,4,7,8,9 are closed and valves 1,2,5,6 opened, and reaction takes place under the conditions for alkylation, then the reaction effluent (alkylated oils) and unreacted isobutane flow into the fractionating tower and are separated with the unreacted isobutane being recycled via the top of tower back to the inlet of reactors and alkylate being discharged from the bottom of tower. When the catalyst in reactor I begins to age, close valves 1 and 5 and open valves 7, 3 and 8; the catalyst is being regenerated with a solvent by washing and extracting in reactor I, the alkylation reaction still continues in reactor II. The used solvent discharged from the reactor I is transferred to a solvent recovery and treatment tank and a regeneration solvent tank for reuse. When the regeneration of catalyst in the reactor I is completed, close valves 7,3 and 8 and open valves 1 and 5 to let alkylation feedstock enter the reactor I, and alkylation reaction proceeds in both reactor I and II. When the catalysts in reactor II begin to age, the same operation is repeated that done for regenerating the catalyst in reactor I. A cycle of the process of alkylation and regeneration is usually about 1,000 hours. The process of regeneration goes on for only more than 10 hours. The aged catalysts resume the activity and selectivity and can be used in alkylation for next running after regeneration, thus ensuring that in the process of the present invention, alkylation is carried out in reactors I and II simultaneously for most of the time.
Figure 2:
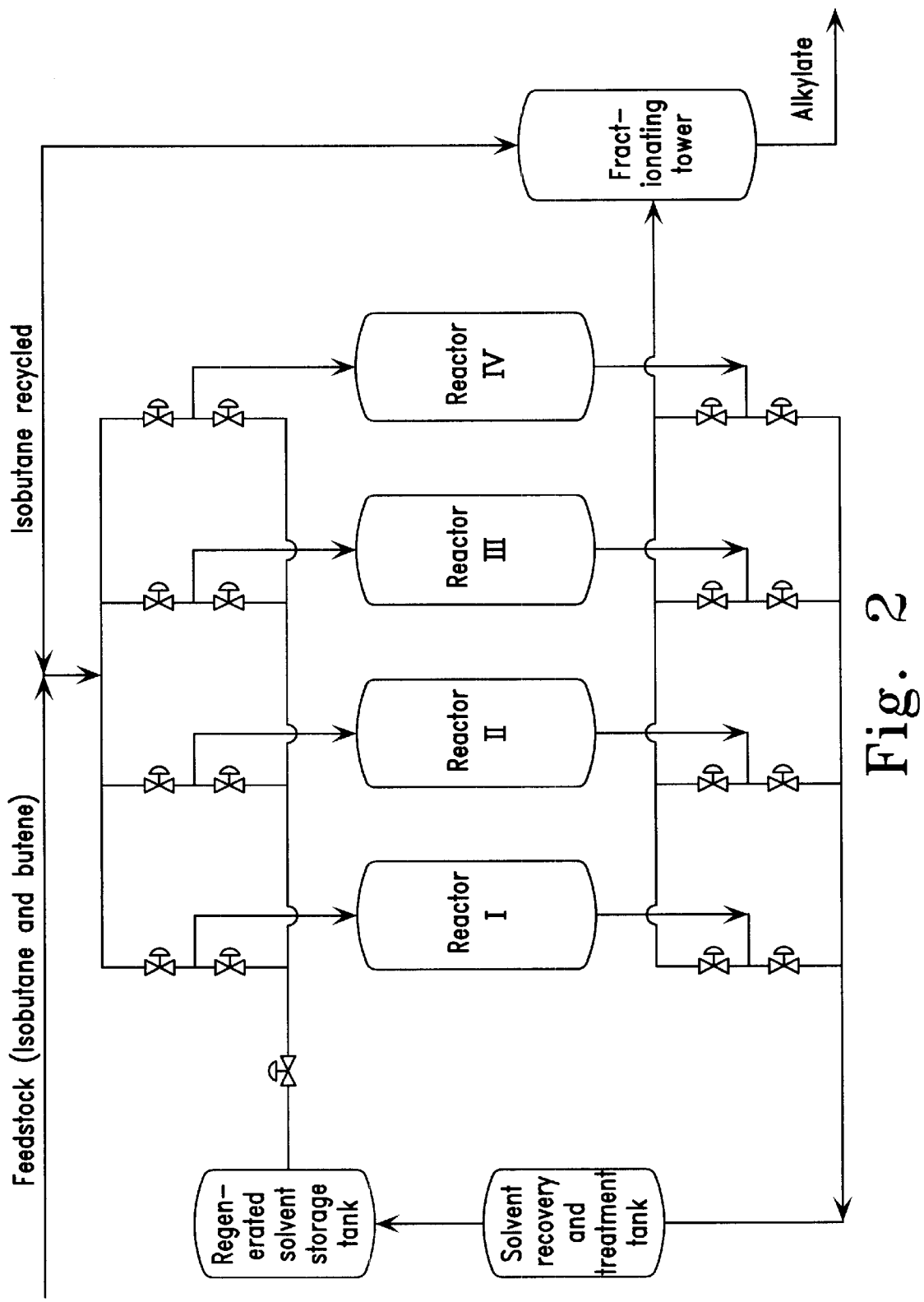
FIG. 2 shows a flow diagram of the alkylation process according to another embodiment of the present invention. There are more than two parallel reactors used in this embodiment, in which the process is operated in the same way as illustrated in the FIG. 1. Feedstock treatment capacity and productivity of alkylated oils can be adjusted flexibly in such reaction system.
Figure 3:
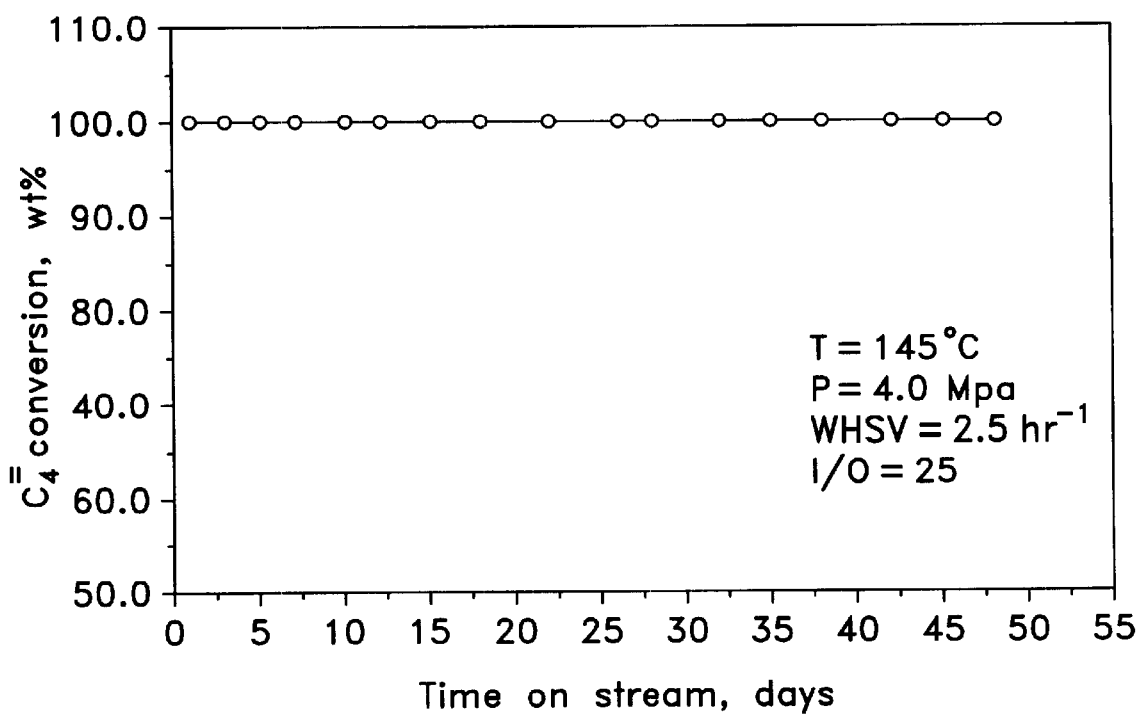
FIG. 3 shows that the activity of catalyst changes with time on stream during the 1400 hours of running in the isobutane-butene alkylation provided in example 1.

The conditions and results of alkylation are shown in FIG. 3. The activity of catalyst ($C_4$-olefin conversion) remained 100% during running for 1400 hours (about 60 days) of alkylation. The octane number (R+M)/2 (R: research octane number; M: motor octane number) of alkylate descended obviously as alkylation proceeded for 68 grams of olefin converted per gram of catalyst. Besides, $C_9^+$ (alkanes with carbon number greater than 9) content in alkylate increased a bit. This result showed that although the activity of the alkylation catalyst did not descend, the selectivity of the catalyst to trimethylpentane became worse. This was called as the aging of the catalyst. It was time to begin the regeneration of the catalyst with a solvent by washing and extracting. The (R+M)/2 data of alkylate were obtained by gas chromatography according the method taught in "Estimate Alkyl yield and Quality", Hydrocarbon Process, Hutson and Logan, 1975, pages 107–108.

When the catalyst began to age, it was regenerated with a solvent by washing and extracting as follows: the temperature and pressure in reactor were reduced and reaction feedstock was discharged; a stream of dry nitrogen was introduced to scavenge the catalyst bed for 2.0~3.0 hours at 60° C. and atmospheric pressure. Then, the temperature was raised to 175° C. and pressure was raised to 5.0 MPa, and a mixture of 50 wt % $C_8$ and 50 wt % $C_{11}$~$C_{15}$ saturated alkanes used as a solvent was pumped into the reactor to wash and extract the catalyst for 15 hours at a WHSV of 2.50 hr 1. As the regeneration was completed, the temperature and pressure in the reactor were descended and the solvent was discharged, then the catalyst was scavenged with a stream of dry nitrogen for 1.0 hour at room temperature and atmospheric pressure. Then, it was ready to proceed to the next cycle of alkylation.

Figure 4:
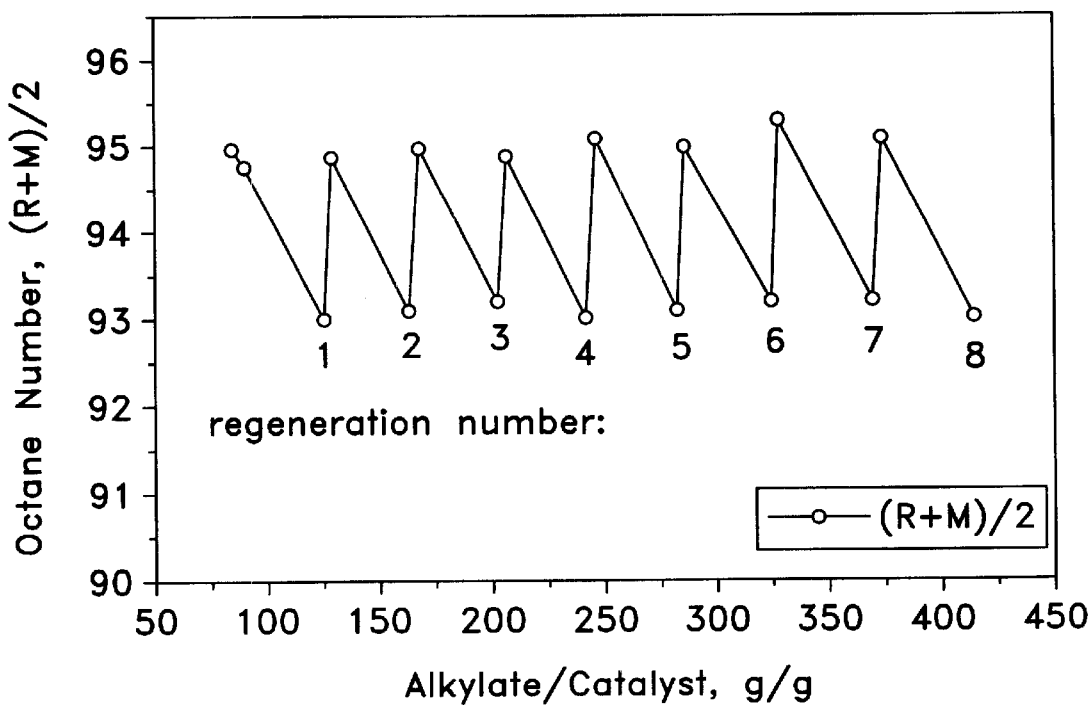
FIG. 4 shows that the octane number of alkylate changes with the amount of alkylate produced in the continuous cycle of the process of alkylation and regeneration provided in example 1.

Alkylation proceeded again in the same way as the beginning of the process after the regeneration of the catalyst was completed. This was called as a cycle of alkylation-regeneration. The cycle of alkylation and regeneration was repeated for 8 times, and the results of cycling of the process are listed in Table 2 and FIG. 4. It can be seen clearly that after regeneration of catalyst with a solvent by washing and extraction, the aged catalyst had resumed completely its selectivity to trimethylpentane and its catalytic activity was restored to the level comparable to that of fresh catalyst.

TABLE 2

| | | $C_9^+$ (wt %) | (R + M)/2 |
|---|---|---|---|
| 1 | beginning | 11.42 | 94.8 |
| | aged | 15.72 | 93.0 |
| 2 | beginning | 11.21 | 94.9 |
| | aged | 15.86 | 93.1 |
| 3 | beginning | 11.09 | 94.7 |
| | aged | 15.70 | 93.0 |
| 4 | beginning | 11.19 | 94.9 |
| | aged | 15.66 | 93.2 |
| 5 | beginning | 10.98 | 95.1 |
| | aged | 15.29 | 93.3 |
| 6 | beginning | 11.36 | 94.8 |
| | aged | 15.64 | 92.9 |
| 7 | beginning | 11.27 | 95.0 |
| | aged | 15.55 | 93.0 |
| 8 | beginning | 11.19 | 94.9 |
| | aged | 15.39 | 93.1 |

Conditions of regeneration by solvent washing and extracting: Temperature: 175°, Pressure: 5.0 MPa, WHSV of solvent: 2.50 hr$^{-1}$.

A supported conjugated Brönsted-Lewis solid super acid catalyst comprising a Brönsted acid of $H_3PW_{12}O_{40}$ and a Lewis acid of $SbF_5$ was used in this example. The catalyst was prepared as follows: 10.0 g of 20% $H_3PW_{12}O_{40}\cdot 2H_2O$/$SiO_2$ catalyst as that prepared in example 1, was loaded in a fixed-bed reactor and was treated with a stream of dry nitrogen at a WHSV of 120 hr$^{-1}$ under 100° C. for 4 hours; then cooled down to 50° C.; a stream of dry nitrogen passed through a lank filled with $SbF_5$, then the nitrogen stream carrying $SbF_5$ passed through the catalyst bed so that $SbF_5$ reacted with the heteropoly acid $H_3PW_{12}O_{40}$ to form the supported conjugated Brönsted-Lewis solid super acid catalyst; finally, the Brönsted-Lewis catalyst was purged with a stream of dry nitrogen for 1 hour, and the supported conjugated Brönsted-Lewis catalyst was obtained and designated as $H_3PW_{12}O_{40}$—$SbF_5/SiO_2$ catalyst.

Alkylation of isobutane with butene mid the regeneration of catalyst were carried out in as the same way as described in example 1. When the catalyst became aged, it was regenerated with solvent at a temperature of 70 C. The cycle of alkylation and regeneration was repeated four times and the $C_9^+$ content and (R+M)/2 data in alkylate were measured at the beginning and ending of each alkylation-regeneration cycle. Results of the four cycles of alkylation and regeneration are listed in Table 3. It can be seen clearly that regeneration in situ of catalyst with solvent by washing and extracting has very good effect on the aged conjugated Brönsted-Lewis solid super acid catalyst.

TABLE 3

| | | $C_9^+$ (wt %) | (R + M)/2 |
|---|---|---|---|
| 1 | beginning | 6.7 | 96.5 |
| | aged | 10.2 | 94.3 |
| 2 | beginning | 6.2 | 96.7 |
| | aged | 10.5 | 94.1 |
| 3 | beginning | 5.4 | 96.4 |
| | aged | 10.1 | 94.0 |
| 4 | beginning | 5.8 | 96.5 |
| | aged | 10.7 | 94.2 |

Condition of regeneration by solvent washing and extracting: Temperature: 70° C., Pressure: 5.0 MPa, WHSV of solvent: 2.50 hr$^{-1}$.

What is claimed is:

1. A process for alkylation of isoparaffin with olefins in at least two parallel alkylation reactors, each reactor containing solid acid catalyst having catalyst activity and catalyst selectivity to alkylates, comprising the steps of:

continuously feeding an alkylation feedstock comprising isoparaffin and mono-olefins into at least one of said parallel alkylation reactors at alkylation conditions to produce alkylate having an octane number, measuring at least one value selected from the group consisting of said catalyst activity, catalyst selectivity, and said produced alkylate octane in said at least one parallel alkylation reactor, and when said measured value descends to a selected value, terminating the continuous feeding of alkylation feedstock from said at least one parallel alkylation reactor, continuously feeding said alkylation feedstock into said at least one of said parallel alkylation reactors at alkylation conditions after regeneration of the acid catalyst, and feeding said alkylation feedstock into another alkylation reactor of said at least two parallel alkylation reactors at alkylation conditions while introducing a solvent stream into the at least one of said parallel alkylation reactors to regenerate the acid catalyst.

2. A process according to claim 1, wherein the isoparaffin in said alkylation feed comprises isobutane and said $C_3$~$C_6$ mono-olefin in said alkylation feed comprises butene.

3. A process according to claim 1, wherein said solid acid catalyst is selected from the group consisting of supported heteropoly acids catalyst, zeolite molecular sieve catalyst, supported conjugated Brönsted-Lewis solid super acid catalyst, ion-exchange resin, and alumina, silica, or zeolitic molecular sieve catalyst treated with Lewis acid.

4. A process according to claim 3, wherein said solid acid catalyst is selected from the group consisting of supported heteropoly acids catalyst, supported conjugated Brönsted-Lewis solid super acid catalyst, and solid polymerized ion-exchange resin.

5. A process according to claim 4, wherein said solid acid catalyst comprises supported heteropoly acids catalyst.

6. A process according to claim 5, wherein said supported heteropoly acids catalyst comprises at least one heteropoly acid having a chemical formula of $H_{8-n}$, wherein A is phosphorus atom or silicon atom, M is tungsten atom or molybdenum atom, n is the number of valence state of A, being 4 or 5 and at least one porous inorganic support material selected from the group consisting of active carbon, silica, alumina, magnesia, titanium dioxide natural or synthetic zeolite, carbon fiber, and clay.

7. A process according to claim 6, wherein said porous inorganic support material is selected from the group consisting of silica, alumina, and mixtures thereof.

8. A process according to claim 3, wherein said solid acid catalyst comprises supported conjugated Brönsted-Lewis solid super acid catalyst and comprises a.) 40~95 wt % of at least one porous inorganic support material selected from the group consisting of active carbon, silica, alumina, magnesia, titanium dioxide, natural or synthetic zeolite, carbon fiber, and clay; b.) 1~60 wt % of at least one heteropoly acid having a chemical formula of $H_{8-n}$, wherein A is phosphorus atom or silicon atom, M is tungsten atom or molybdenum atom, n is the number of valence state of A, being 4 or 5 and c.) 0.3~15 wt % of at least one Lewis acid selected from the group consisting of $AICl_3$, $BF_3$ and $XF_5$, wherein X is P, As, Sb, or Bi.

9. A process according to claim 1, wherein said solvent stream comprises at least one solvent selected from the group consisting of $C_4$~$C_{20}$ saturated fatty hydrocarbons, aromatics, alcohols, phenols, ethers, esters, alkane halides, and $CS_2$.

10. A process according to claim 9, wherein said solvent stream comprises at least one $C_4$~$C_{16}$ saturated fatty hydrocarbons.

11. A process according to claim 10, wherein said solvent stream comprises at least one $C_5$~$C_{12}$ saturated fatty hydrocarbons.

12. A process according to claim 9, wherein said solvent stream comprises at least one $C_2$~$C_8$ alcohols, $C_2$~$C_8$ esters or $C_1$~$C_4$ alkanes halide.

13. A process according to claim 1, wherein said alkylation conditions comprise supercritical reaction conditions.

14. A process according to claim 13, wherein said supercritical reaction conditions comprise a reaction temperature in the range of from the supercritical temperature of isoparaffin to 300° C.; a reaction pressure in the range of from the supercritical pressure of isoparaffin to 10.0 MPa; the mole ratio of isoparaffin to olefin in the alkylation feedstock is in the range of 2.0~100; and a WHSV of alkylation feedstock in the range of 0.1~20 $hr^{-1}$.

15. A process according to claim 14, wherein said supercritical reaction conditions comprise a reaction temperature in the range of from the supercritical temperature of isoparaffin to 250° C.; a reaction pressure in the range of from the supercritical pressure of isoparaffin to 9.0 MPa; a mole ratio of isoparaffin to olefin in the alkylation feedstock is in the range of 10~90; and a WHSV of alkylation feedstock in the range of 0.5~8.0 $hr^{-1}$.

16. A process according to claim 15, wherein said reaction temperature is in the range of from the supercritical temperature of isoparaffin to 200° C.; and said reaction pressure is in the range of from the supercritical pressure of isoparaffin to 6.0 MPa.

17. A process according to claim 1, wherein the step of introducing said solvent stream into said at least one parallel alkylation reactor to regenerate solid acid catalysts contained therein further comprises separating the alkylation feedstock from the solid acid catalysts and washing the solid acid catalysts for 0.2~24 hrs with said solvent stream under the conditions of a temperature of 25~300° of 0~8.0 MPa, and a WHSV of 0.1~20.0 $hr^{-1}$.

18. A process according to claim 17, wherein the step of introducing a solvent stream into said at least one parallel alkylation reactor to regenerate solid acid catalysts contained therein further comprises separating the alkylation feedstock, from the solid acid catalysts and washing the solid acid catalysts for 0.5~15 hrs with said solvent stream under the conditions of a temperature of 50~200 C., a pressure of 0.2~6.0 MPa, and a WHSV of 0.5~8.0 $hr^{-1}$.

19. A process according to claim 1, wherein the mono-olefins in said alkylation feed comprise $C_3$–$C_6$ mono-olefins.

20. A process according to claim 1 further including the step of withdrawing said solvent stream from said at least one parallel alkylation reactor after said solvent stream has contacted said solid acid catalysts and transferring said solvent stream to a solvent-recovery unit for recovery of said solvent.

21. A process for alkylation of isoparaffin with olefins in at least two parallel alkylation reactors, each reactor containing solid acid catalyst having catalyst activity and catalyst selectivity to alkylates, comprising the steps of:

feeding an alkylation feedstock comprising isoparaffin and mono-olefins into at least one of said parallel alkylation reactors at alkylation conditions comprise supercritical reaction conditions to produce alkylate having an octane number, measuring at least one value selected from the group consisting of said catalyst activity, catalyst selectivity, and said produced alkylate octane in said at least one parallel alkylation reactor, and when said measured value descends to a selected value, terminating the feeding of alkylation feedstock from said at least one parallel alkylation reactor, feeding said alkylation feedstock into said at least one of said parallel alkylation reactors at alkylation conditions after regeneration of the acid catalyst, and feeding said alkylation feedstock into another alkylation reactor of said at least two parallel alkylation reactors at alkylation conditions comprise supercritical reaction conditions while introducing a solvent stream into the at least one of said parallel alkylation reactors to regenerate the acid catalyst.

* * * * *